(12) United States Patent
Horn-Wyffels (10) Patent No.: US 8,126,571 B2
(45) Date of Patent: Feb. 28, 2012

(54) EXPANDABLE ASSEMBLY FOR CARDIAC LEAD FIXATION

(75) Inventor: Mitchell L. Horn-Wyffels, New Hope, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 316 days.

(21) Appl. No.: 12/484,484

(22) Filed: Jun. 15, 2009

(65) Prior Publication Data

US 2009/0319015 A1    Dec. 24, 2009

Related U.S. Application Data (60) Provisional application No. 61/074,768, filed on Jun. 23, 2008.

(51) Int. Cl.
*A61N 1/05* (2006.01)

(52) U.S. Cl. ........................................ 607/126

(58) Field of Classification Search ........... 607/126–128
See application file for complete search history.

(56) References Cited

U.S. PATENT DOCUMENTS

| | | | | |
|---|---|---|---|---|
| 4,280,512 A * | 7/1981 | Karr et al. | ...................... | 607/128 |
| 4,317,459 A | 3/1982 | Gilman | | |
| 4,471,777 A * | 9/1984 | McCorkle, Jr. | ................ | 606/129 |
| 4,913,164 A * | 4/1990 | Greene et al. | .................. | 607/126 |
| 4,957,118 A * | 9/1990 | Erlebacher | ..................... | 607/128 |
| 4,988,347 A * | 1/1991 | Goode et al. | ....................... | 606/1 |
| 5,006,104 A * | 4/1991 | Smith et al. | ...................... | 600/16 |
| 5,117,828 A * | 6/1992 | Metzger et al. | ............... | 600/380 |
| 5,207,683 A * | 5/1993 | Goode et al. | ................... | 606/108 |
| 5,238,007 A * | 8/1993 | Giele et al. | ...................... | 607/126 |
| 5,239,999 A * | 8/1993 | Imran | ............................. | 600/374 |
| 5,304,120 A * | 4/1994 | Crandell et al. | .............. | 604/501 |
| 5,344,439 A * | 9/1994 | Otten | ............................. | 607/126 |
| 5,378,239 A | 1/1995 | Termin et al. | | |
| 5,603,694 A | 2/1997 | Brown et al. | | |
| 6,136,021 A | 10/2000 | Tockman et al. | | |
| 6,161,029 A | 12/2000 | Spreigl et al. | | |
| 6,322,559 B1 * | 11/2001 | Daulton et al. | .................. | 606/41 |
| 6,438,427 B1 | 8/2002 | Rexhausen et al. | | |
| 6,611,710 B2 * | 8/2003 | Gomperz et al. | .................. | 607/7 |
| 6,611,721 B1 * | 8/2003 | Witte et al. | ..................... | 607/126 |
| 6,711,443 B2 | 3/2004 | Osypka | | |
| 6,741,893 B2 | 5/2004 | Smits | | |
| 6,763,270 B1 * | 7/2004 | Gomperz et al. | ............. | 607/126 |
| 6,823,217 B2 | 11/2004 | Rutten et al. | | |
| 6,909,920 B2 | 6/2005 | Lokhoff et al. | | |
| 6,968,237 B2 | 11/2005 | Doan et al. | | |
| 7,076,309 B2 | 7/2006 | Hine et al. | | |

(Continued)

FOREIGN PATENT DOCUMENTS

WO    WO 2004/028618 A1    4/2004

(Continued)

*Primary Examiner* — Kennedy Schaetzle
(74) *Attorney, Agent, or Firm* — Faegre Baker Daniels LLP (57) ABSTRACT

A cardiac lead includes a lead body that defines a passage, a conductive element that extends through the passage, and a fixation assembly. The fixation assembly includes a threaded member threadably engaged with the conductive element such that rotation of the threaded member causes the threaded member to translate longitudinally relative to the conductive element. A fixation element has a first end coupled to the threaded member and a second end coupled to a fixed location. A resilient membrane extends over the fixation element such that rotation of the threaded member affects the resilient membrane radially with respect to the conductive element.

19 Claims, 6 Drawing Sheets

U.S. PATENT DOCUMENTS

| | | |
|---|---|---|
| 7,107,105 B2 | 9/2006 | Bjorklund et al. |
| 7,139,614 B2 | 11/2006 | Scheiner et al. |
| 7,155,292 B2 | 12/2006 | Kawula et al. |
| 7,328,071 B1 | 2/2008 | Stehr et al. |
| 7,330,765 B2 | 2/2008 | Haldeman |
| 2002/0161423 A1 | 10/2002 | Lokhoff et al. |
| 2003/0220676 A1 | 11/2003 | Helland |
| 2004/0059404 A1 | 3/2004 | Bjorklund et al. |
| 2004/0243210 A1 | 12/2004 | Morgan et al. |
| 2005/0070981 A1 | 3/2005 | Verma |
| 2005/0080472 A1 | 4/2005 | Atkinson et al. |
| 2006/0095078 A1 | 5/2006 | Tronnes |
| 2008/0077220 A1 | 3/2008 | Reddy |
| 2008/0147160 A1 | 6/2008 | Ghione et al. |
| 2008/0183267 A1 | 7/2008 | D'Aquanni et al. |

FOREIGN PATENT DOCUMENTS

| | | |
|---|---|---|
| WO | WO 2006/132702 A1 | 12/2006 |

* cited by examiner

EXPANDABLE ASSEMBLY FOR CARDIAC LEAD FIXATION

CROSS-REFERENCE TO RELATED APPLICATION

This application claims priority to Provisional Application No. 61/074,768, filed Jun. 23, 2008, which is herein incorporated by reference in its entirety.

TECHNICAL FIELD

The present invention relates to medical device leads. More specifically, the invention relates to fixation of a medical device lead within a patient's coronary vasculature.

BACKGROUND

Cardiac function management systems are used to treat arrhythmias and other abnormal heart conditions. Such systems generally include cardiac leads, which are implanted in or about the heart, for delivering an electrical pulse to the cardiac muscle, for sensing electrical signals produced in the cardiac muscle, or for both delivering and sensing. The lead typically consists of a flexible conductor, defining a central channel or lumen, surrounded by an insulating tube or sheath extending from an electrode at the distal end to a connector pin at the proximal end.

Cardiac lead placement may be accomplished by introducing the lead through a major blood vessel and advancing a distal end of the lead to a final destination in or near the heart. To facilitate cannulation of the vasculature, it is often helpful to first advance a guiding catheter through the desired vascular path. One difficulty with implanting leads in this fashion is that the cardiac lead has a tendency to become dislodged from its desired location during or after lead implantation. For example, when a clinician withdraws the guiding catheter, the lead may dislodge or otherwise reposition. Cardiac leads may also become dislodged by subsequent physiological activity. Furthermore, after an extended implantation period, tissue in-growth or vasculature restructuring around the lead may prevent the lead from being repositioned within or removed from the patient's vasculature.

SUMMARY

The present invention relates to a cardiac lead that includes a lead body that defines a passage, a conductive element that extends through the passage, and a fixation assembly. The fixation assembly includes a threaded member threadably engaged with the conductive element such that rotation of the threaded member causes the threaded member to translate longitudinally relative to the conductive element. A fixation element has a first end coupled to the threaded member and a second end coupled to a fixed location. A resilient membrane is over the fixation element such that rotation of the threaded member affects the resilient membrane radially with respect to the conductive element.

In another embodiment of the present invention, the fixation assembly includes a threaded member threadably engaged with the conductive element, and an expandable mechanism coupled to the threaded member. The expandable mechanism is configured to transition between a retracted configuration and an expanded configuration when the threaded member is rotated.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
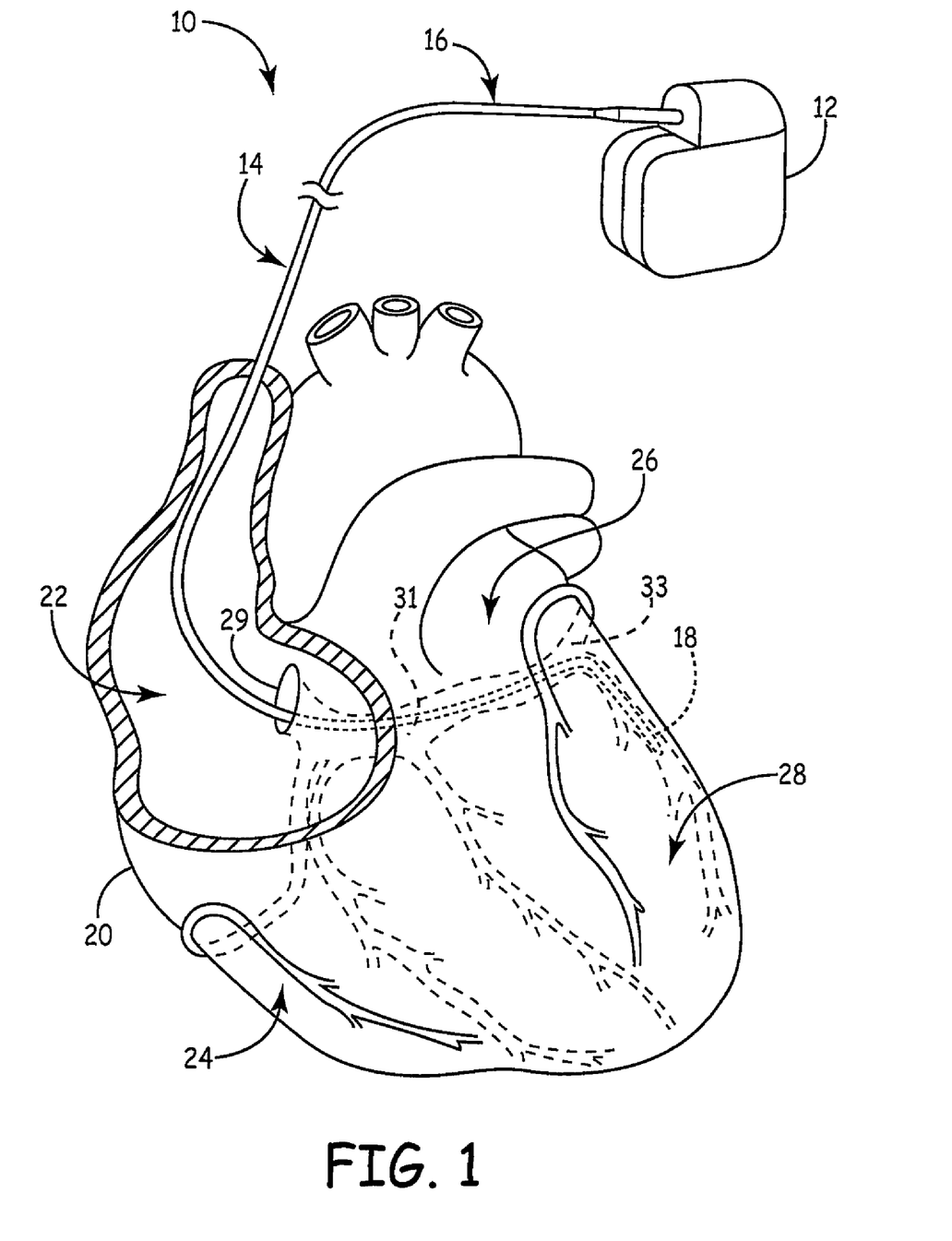
FIG. 1 is a schematic view of a cardiac lead implanted in a cardiac vessel.

FIG. 1 is a schematic view of a cardiac rhythm management system 10 including a pulse generator 12 coupled to a lead 14 having a proximal end 16 and a distal end 18. As shown in FIG. 1, distal portions of the lead 14 are disposed in a patient's heart 20, which includes a right atrium 22, a right ventricle 24, a left atrium 26, and a left ventricle 28. In the embodiment illustrated in FIG. 1, a distal end 18 of the lead 14 is transvenously guided through the right atrium 22, through the coronary sinus ostium 29, and into a branch of the coronary sinus 31 or the great cardiac vein 33. The illustrated position of the lead 14 can be used for sensing or for delivering pacing and/or defibrillation energy to the left side of the heart 20, or to treat arrhythmias or other cardiac disorders requiring therapy delivered to the left side of the heart 20. Additionally, it will be appreciated that the lead 14 can also be used to provide treatment in other regions of the heart 20 (e.g., the right ventricle).

Figure 2:
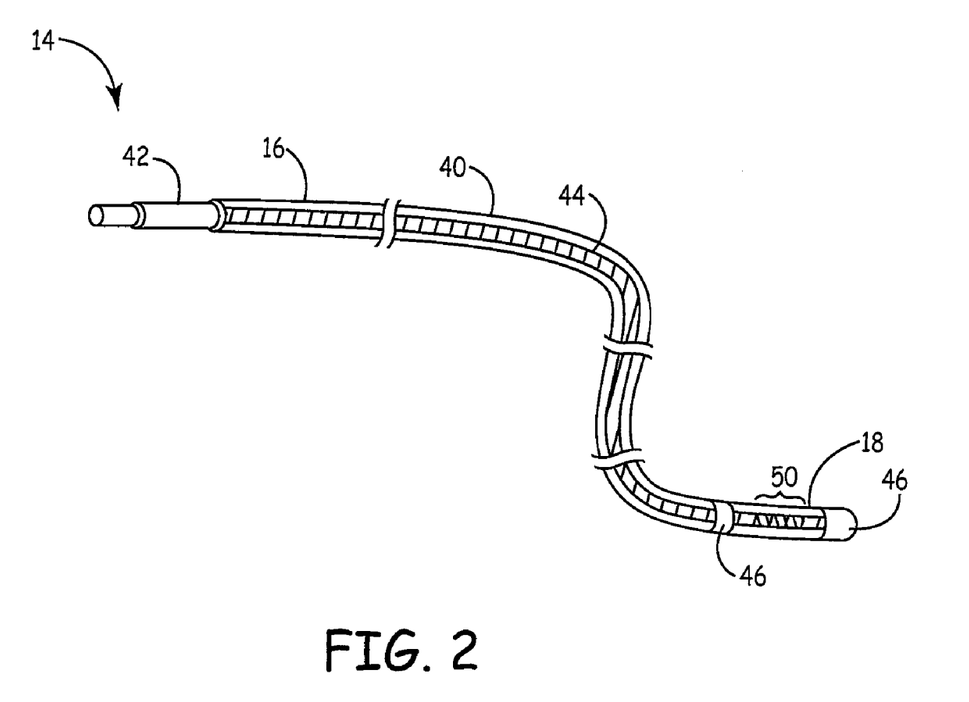
FIG. 2 is a partial cross-section view of the cardiac lead shown in FIG. 1.

FIG. 2 is a partial cross-sectional view of the lead 14 suitable for use with the present invention. The lead 14 includes an elongated, insulative lead body 40 extending from the proximal end 16 to the distal end 18. The proximal end 16 is configured to be operatively connected to the pulse generator 12 (FIG. 1) via the connector 42. At least one conductor 44 extends from the connector 42 at the proximal end 16 to one or more electrodes 46 at the distal end 18 of the lead 14. In some embodiments, the conductor 44 is a coiled or helical conductor, and in the case of multiple conductors 44, the conductors are arranged in a co-radial configuration.

The lead body 40 is flexible, but substantially non-compressible along its length, and has a circular cross-section. According to one embodiment, an outer diameter of the lead body 40 ranges from about 2 to about 10 French. The lead 14 may be unipolar, bipolar, or multi-polar depending upon the type of therapy to be delivered and/or the therapeutic needs of the patient. In embodiments of the present invention employing multiple electrodes 46 and multiple conductors 44, each conductor 44 is adapted to be connected to an individual electrode 46 in a one-to-one manner allowing each electrode 46 to be individually addressable. Additionally, the lead body 40 can include one or more lumens. In some embodiments at least one lumen is adapted to receive the insertion of the conductor 44 during construction of the lead 14. In further embodiments, at least one lumen is adapted to receive a guiding element such as a guidewire or a stylet for delivery of the lead 14 to a target location within a patient's heart.

The electrodes 46 can have any electrode configuration as is known in the art. According to one embodiment of the present invention, at least one electrode 46 can be a ring or partial ring electrode. According to another embodiment, at least one electrode 46 is a shocking coil. According to yet another embodiment of the present invention, at least one electrode 46 includes exposed and unexposed electrode portions. In some embodiments, a combination of electrode configurations may be used. The electrodes 46 can be coated with or formed from platinum, stainless steel, MP35N, a platinum-iridium alloy, palladium, a palladium alloy, titanium, tantalum, a tantalum alloy, a metal oxide (e.g., IrO), or another similar conductive material. The electrodes 46 may also be coated with a coating that elutes a pharmaceutical, such as a steroid. In further embodiments, a drug-delivery element (e.g., a steroid-eluting collar) may be located adjacent to at least one electrode 46.

According to the present invention, the lead 14 includes a fixation element 50 for securing and stabilizing the lead 14 at a target site within a patient's body. In some embodiments, the fixation assembly is disposed proximate the distal end 18 of the lead 14. As described in the following figures, the fixation assembly of the present invention is membrane covered to provide fixation of the lead 14 to a patient's vasculature with limited tissue in-growth. Consequently, if the lead 14 is to be removed from or repositioned in the patient, the fixation assembly may be retracted without damaging the patient's vasculature.

Figure 3:
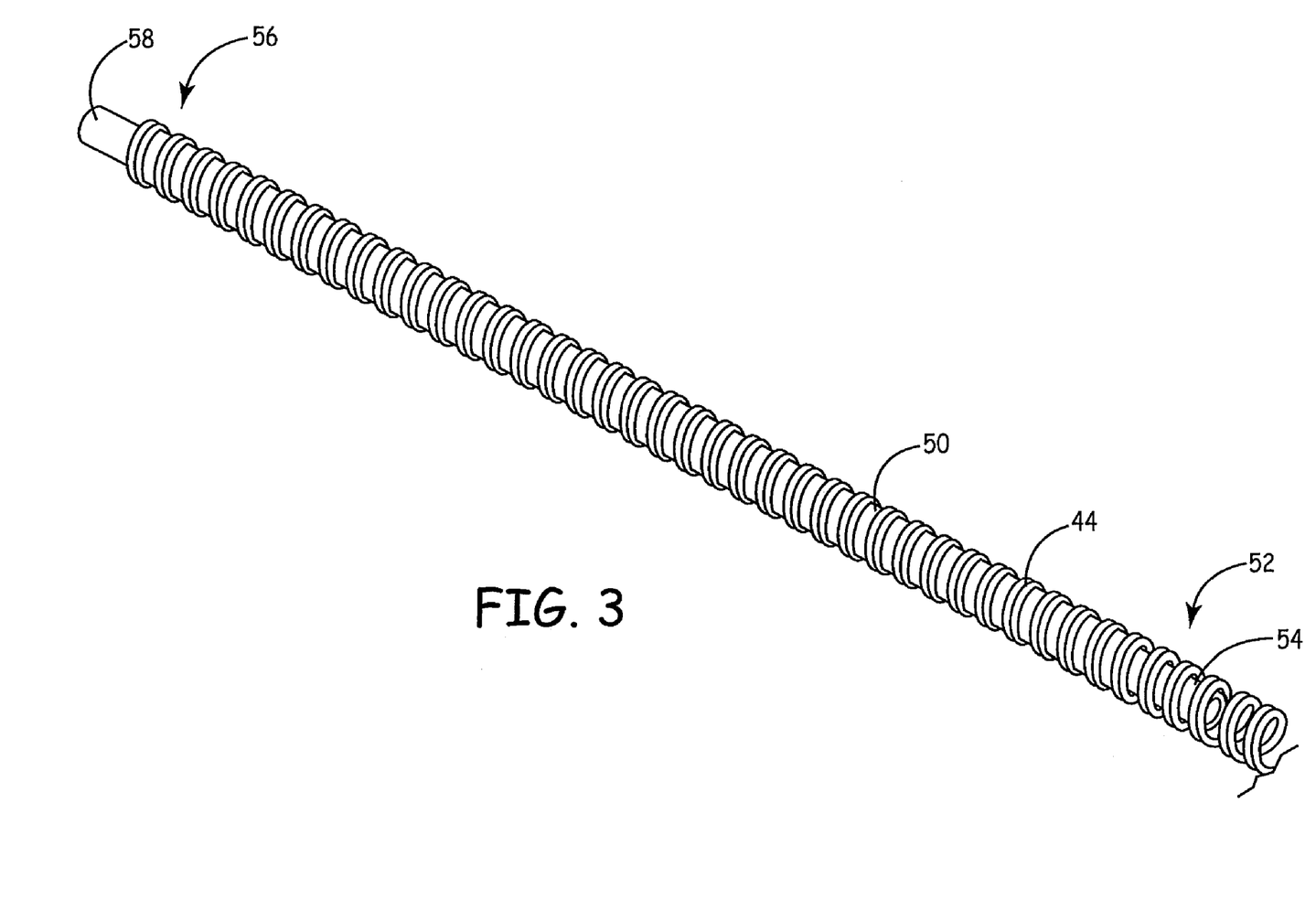
FIG. 3 is a perspective view of a fixation element according to an embodiment of the present invention in a contracted configuration.

FIG. 3 is a perspective view of the conductor 44 including the fixation element 50 according to an embodiment of the present invention. In the embodiment shown, the fixation element 50 has a coiled or helical configuration. The fixation element 50 is arranged such that turns of the fixation element 50 are interleaved or interwound with turns of the conductor 44 when in the contracted configuration shown in FIG. 3. While the conductor 44 is shown as a bifilar coil (i.e., two closely spaced, parallel windings), it will be appreciated that the principles of the present invention also apply to monofilar coils or other multifilar configurations with more than two filars.

The fixation element 50 includes a first end 52, which is coupled to a threaded member 54, and a second end 56, which is coupled to a fixed location 58. In some embodiments, the fixation element 50 is coupled to the threaded member 54 by securably attaching (e.g., welding, crimping bonding, molding, etc.) the first end 52 with the threaded member 54. In other embodiments, the fixation element 50 is coupled to the threaded member 54 by integrating the fixation element 50 at the first end 52 with the threaded member 54. For example, a small pitched, tightly wound element could be connected between the fixation element 50 and the threaded member 54 to allow the joint between the threaded member 54 and the fixation element 50 to torsionally relax the stress between the members. In further embodiments, the threaded member 54 is formed integrally with and made of the same material as the fixation element 50. In this case, the transition between the fixation element 50 and the threaded member 54 would flex to relieve stress between the two members.

The second end 56 of the fixation element 50 may be coupled to the fixed location 58 using any of the means described to secure the first end 52 to the threaded member 54, or using any other suitable means not specifically described. The fixed location 58 is an element that remains fixed relative to the fixation element 50 and the threaded member 54 during expansion and retraction of the fixation element 50. The fixed location 58 may be secured to any of the lead body 40, the conductor 44, or the electrodes 46 to prevent the fixed location 58 from moving relative to the conductor 44.

The fixation element 50 may be formed from a variety of elastic or super-elastic materials having any suitable cross sectional shape and the ability to provide radial force with minimal bending stress. In some embodiments, the fixation element 50 is comprised of a nickel-titanium alloy, such as Nitinol. In other embodiments, the fixation element 50 is comprised of materials including, but not limited to, bio-compatible polymers, bio-resorbable polymers, polyurethane, titanium, MP35N, platinum and platinum alloys, a spring steel such as spring temper 316 SS, polyetheretherketone (PEEK), and combinations thereof. Other materials known in the art can also be used to form the fixation element 50. The material or combination of materials should be selected such that the fixation element 50 has a high elasticity range, thereby allowing the fixation element 50 to expand and collapse without plastic deformation. The fixation element 50 may also be heat treated by known methods to improve the elasticity and/or strength of the fixation element 50. In some embodiments, the fixation element 50 is made of a non-conductive material to minimize interference with operation of the conductor 44. Alternatively, the fixation element 50 may be made of a conductive material, such as a conductive metal, to deliver pacing or sensing signals to and from the electrodes 46 or to act as an electrode itself.

The threaded member 54 is configured such that rotation of the threaded member 54 causes the threaded member 54 to translate longitudinally relative to the conductor 44 and unwind the fixation element 50. In some embodiments, the threaded member 54 is a screw or other threaded mechanism. The threaded member 54 is disposed inside a lumen defined by turns of the conductor 44, and is sized such that an exterior of the threaded member 54 (or portions thereof) engages portions of the conductor 44 that define the lumen. For example, in one embodiment, the threaded member 54 is a screw that includes external threads or grooves sized to match the pitch of the conductor 44 so as to threadably engage with the conductor 44. In other words, the conductor 44 effectively acts as a threaded hole for the screw, and the threads of the screw engage the filar(s) of the conductor 44.

When the threaded member 54 is rotated, turns of the fixation element 50 unwind from between turns of the conductor 44. This, coupled with the longitudinal translation of the threaded member 54 relative to the conductor 44, causes the fixation element 50 to expand radially with respect to the conductor 44. In some embodiments, the fixation element 50 has a normally-open configuration in which the lead 14 is introduced with the fixation element 50 in a contracted configuration, and a seal is broken by actuating the threaded member 54 to release the fixation element 50 into its normally-open state. In other embodiments, the fixation element 50 has a normally-closed configuration, wherein the threaded member 54 is locked into position when the fixation element 50 is fully expanded, and releasing the lock causes the fixation element 50 to return to its normally closed state.

As the fixation element 50 expands, the lead body 40 (or a resilient membrane formed over the fixation element 50) is forced radially outward around the fixation element 50. With continued rotation of the threaded member 54, the diameter of the fixation element 50 increases until the fixation element 50 reaches its fully expanded configuration. When fully expanded, the fixation element 50 confronts the patient's vasculature with sufficient outward radial force to the secure lead 14 in the vasculature. The fixation element 50 in its fully expanded configuration will be described in more detail with regard to FIGS. 5 and 6.

When the cardiac lead 14 is disposed in the patient's vasculature, the threaded member 54 may be rotated to expand the fixation element 50 in a variety of ways. In some embodiments, the threaded member 54 is adapted to engage an actuating device that is operable to rotate the threaded member 54. For example, as described above, a guidewire may be employed for delivery of the lead 14 to a target location within a patient's heart. The guidewire may include a feature or features that interlock or engage with a hole, slot, notch, or other feature on the threaded member 54. Once the guidewire is interlocked or engaged with the threaded member 54, the surgeon or medical professional can manipulate the guidewire to rotate the threaded member 54 to expand or collapse the fixation element 50. Alternatively, the guidewire used to deliver the lead 14 to the target location may be withdrawn and a stylet including features that engage the threaded member 54 can be introduced to expand or retract the fixation element 50.

Figure 4A:
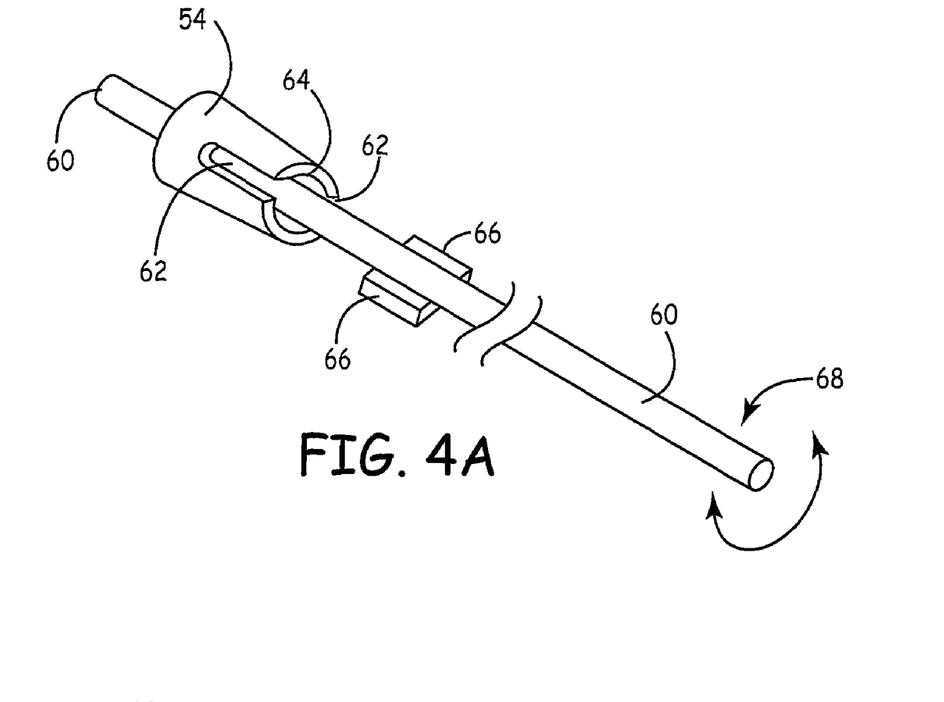
FIGS. 4A and 4B are perspective views of exemplary embodiments of a threaded member operable to radially affect the fixation element shown in FIG. 3.
Figure 4B:
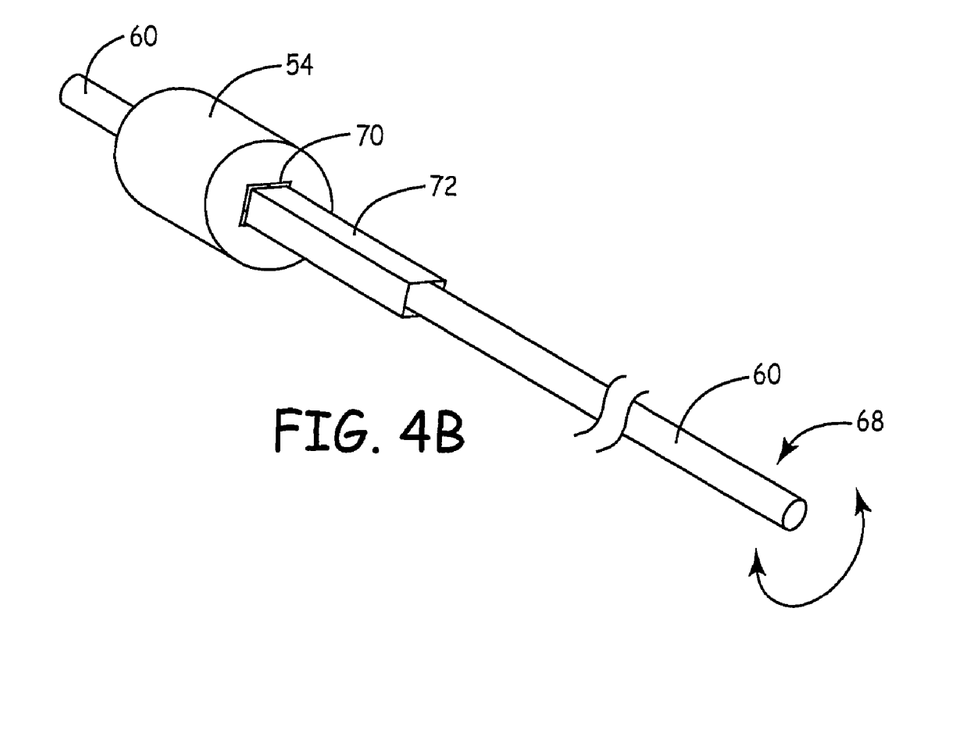

FIGS. 4A and 4B are perspective views of exemplary embodiments of the threaded member 54 including features that are configured to engage with the actuating device 60. The actuating device 60 may be a stylet or guidewire, for example. In the embodiment shown in FIG. 4A, the threaded member 54 includes opposing slots 62 formed from a front edge 64 along the threaded member 54. The actuating device 60 includes opposing tabs 66 formed on an exterior surface of the actuating device 60. In some embodiments, the tabs 66 are formed integrally with the actuating device 60. In other embodiments, the tabs 66 are secured to the actuating device 60 (e.g., by welding or adhering the tabs 66 to the actuating device 60) or machined directly onto the actuating device 60. The actuating device 60 is passed through the lumen of the conductor 44 until the tabs 66 engage the slots 62 to form an interlocking assembly. A surgeon or other medical professional may then manipulate the actuating device 60 at the proximal end 68, such as by rotating the actuating device 60 as shown. The direction of rotation of the actuating device 60 determines the direction that the threaded member 54 translates along the conductor 44 and, consequently, whether fixation element expands or contracts.

In the embodiment shown in FIG. 4B, the threaded member 54 includes female feature 70, and the actuating device 60 includes a male feature 72. To engage the threaded member 54, the actuating device 60 is passed through the lumen of the conductor 44 until the male feature 72 mates with the female feature 70 to form an interlocking assembly. A medical professional can manipulate the actuating device 60 from the proximal end 68 to rotate the threaded member 54. While the female feature 70 is shown as a square- or rectangular-shaped aperture, and the male feature 72 is shown as a square or rectangular spline, the female feature 70 and the male feature 72 may be in any form that can be mated and can generate torque on the threaded member 54 when the actuating device 60 is manipulated.

It will be appreciated that the configurations for the threaded member 54 and the actuating device 60 shown in FIGS. 4A and 4B are merely examples, and variations on these designs are possible. For example, the actuating device 60 is shown engaging the threaded member 54 from the side that the actuating device 60 first encounters when passed through the lumen of the conductor 44. Alternatively, the features on the actuating device 60 may be configured to pass through the threaded member 54 to engage the opposite side of the threaded member 54 when pulled back through the lumen. In this way, the threaded member 54 would translate away from the distal end 56 when expanding the fixation element 50. In addition, a locking mechanism may be included in the fixation assembly to engage the fixation element 50 and/or the threaded member 54 to further secure the fixation element 50 when the fixation element 50 is in a fully expanded configuration.

Figure 5:
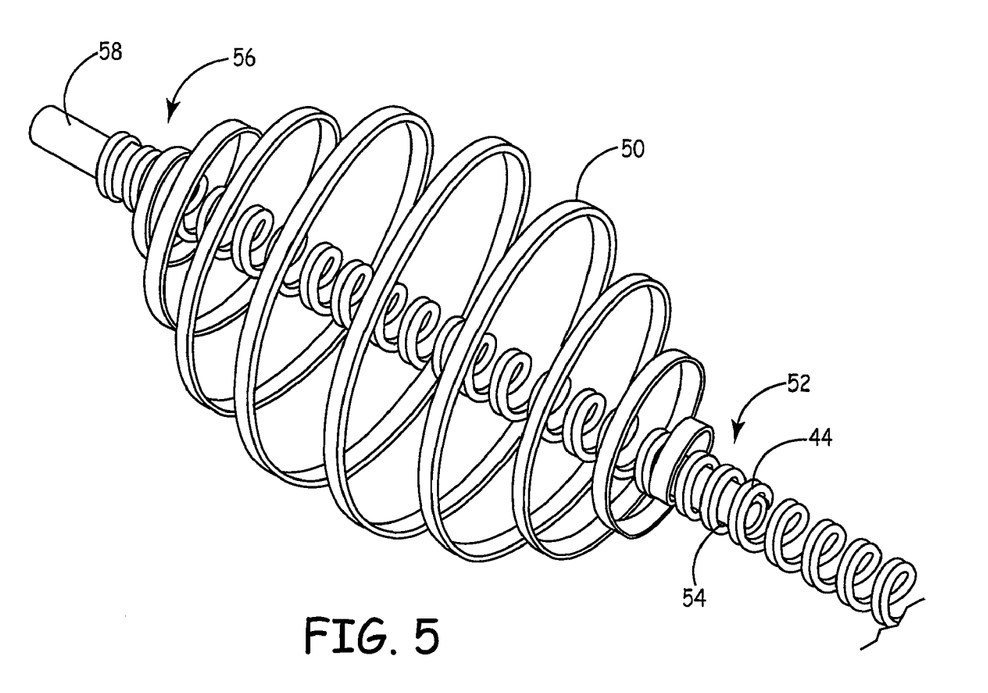
FIG. 5 is a perspective view of the fixation element according to an embodiment of the present invention in an expanded configuration.
Figure 6:
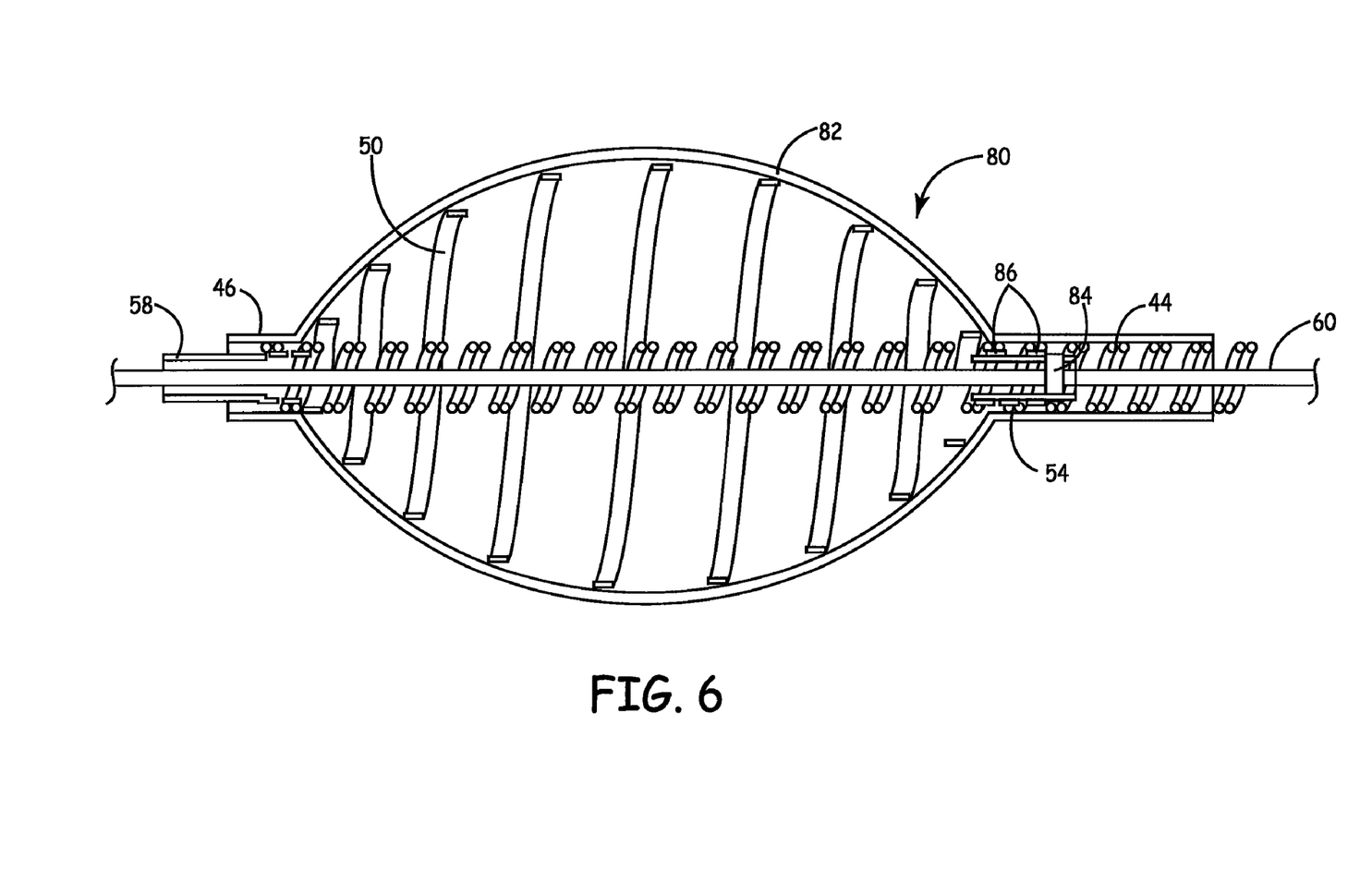
FIG. 6 is a cross-section view of a fixation assembly according to an embodiment of the present invention in an expanded configuration and engaged with an actuating member.

FIG. 5 is a perspective view of the fixation element 50 according to an embodiment of the present invention in an expanded configuration. FIG. 6 is a cross-section view of a fixation assembly 80 according to an embodiment of the present invention in an expanded configuration. The fixation assembly 80 includes the fixation element 50 and a membrane 82 extending over the fixation element 50. FIG. 6 shows the actuating device 60 with a feature 84 (e.g., the tabs 66 in FIG. 4A or the male feature 72 in FIG. 4B) engaged with the threaded member 54. Also shown in FIG. 6 is the electrode 46, which may be either of the electrodes 46 shown in FIG. 2, and to which the conductor 44 delivers sensing and/or pacing signals.

When the actuating device 60 is engaged with the threaded member 54, manipulation of the actuating device 60 causes the threaded member 54 to rotate. As shown in FIG. 6, the threaded member 54 includes threads 86 that engage the conductor 44 such that rotation of the threaded member 54 causes the threaded member 54 to translate longitudinally along the center axis of the conductor 44. The threaded member 54 translates between a first axial position when the fixation element 50 is in the collapsed configuration shown in FIG. 3, and a second axial position when the fixation element 50 is in the expanded configuration shown in FIGS. 5 and 6.

When the threaded member 54 is rotated in a direction to expand the fixation element 50, turns of the fixation element 50 unwind from between turns of the conductor 44. As turns of the fixation element 50 unwind and the threaded member 54 translates longitudinally along the conductor 44, the turns radially expand relative to the conductor 44. The turns substantially equidistant between the threaded member 54 and the fixed location 58 have the largest radial expansion, with each turn closer to the threaded member 54 and the fixed location 58 having a smaller radial expansion.

As the fixation element 50 expands, the turns of the fixation element 50 confront an inner surface of the membrane 82. With increased expansion, the force of the fixation element 50 against the membrane 82 causes the membrane 82 to deflect radially with respect to the conductor 44. When fully expanded, the membrane 82 confronts the walls of the patient's vasculature with enough outward force to secure the lead 14 in the vasculature. The membrane 82 isolates the fixation element 50 from the patient's vasculature, thereby preventing tissue in-growth with the fixation element 50.

The membrane 82 may be formed integrally with the lead body 40, and may be made of the same material as the lead body 40, or a different material than the lead body 40. In some embodiments, the membrane 82 is comprised of an elastic biocompatible material that provides minimal resistance to expansion of the fixation element 50, while having sufficient durability to endure abrasive friction with the fixation element 50 as the fixation element 50 rotates and expands. Examples of materials having these properties include silicone, polytetrafluoroethylene (PTFE), and polyurethane. In embodiments in which the fixation member 50 is configured for pacing and/or sensing, the membrane 82 may be porous and/or include a conductive material.

An advantage of the present invention is that the membrane 82 prevents permanent in-growth into the lead body 40 or the fixation element 50. Consequently, the fixation element 50 can be retracted, if necessary, to allow extraction of the lead 14 from or repositioning of the lead 14 in the patient's vasculature with decreased risk of damage to the adjacent tissue. The fixation element 50 can be retracted in much the same way as it was originally deployed by engaging the actuating member 60 with the threaded member 54. The actuating member 60 can then be manipulated to rotate the threaded member 54 in a direction that retracts the fixation element 50.

When retracting the fixation element 50, it may be desirable to more permanently engage the actuating member 60 with the threaded member 54, especially for extraction of the lead 14. This would allow the actuating member 60 and the lead 14 to be withdrawn from the patient's vasculature when the fixation element 50 is fully retracted. The actuating member 60 may be affixed to the threaded member 54 in a variety of ways. For example, the actuating member 60 may include a gradual taper in the region including the feature 84, which would allow the actuating member 60 to be forcibly fixed to the threaded member 54. The actuating member 60 may also be welded or bonded (e.g., with an epoxy or adhesive) to the threaded member 54 to affix these two elements together. Furthermore, the actuating member 60 may be designed to pass through the threaded member 54, and then turned to an alternate orientation that prevents the actuating member 60 from being withdrawn back through the lumen of the conductor 44.

It will be appreciated that variations on the embodiments described above are contemplated by the present invention. In one alternative embodiment, the membrane 82 is eliminated and the fixation element 50 is comprised of a conductive material to employ the fixation element 50 as a pacing electrode. In other words, when the fixation element 50 is fully expanded, turns of the fixation element 50 in contact with the patient's vasculature are operable as pacing electrodes, to which pacing signals are delivered by the conductor 44. In order to prevent tissue in-growth, a thin layer of biocompatible material that does not affect pacing performance may be formed over the fixation element 50. Examples of materials that may be used for this purpose include ethylene tetrafluoroethylene (ETFE) or polytetrafluoroethylene (PTFE), which may be modified to include pores to improve pacing performance.

In another alternative embodiment, the fixation assembly 80 is designed to expand non-symmetrically with respect to the conductor 44. To accomplish this, a non-symmetrical membrane 82 (e.g., with varying thickness) may be formed over the fixation element 50 that forces the fixation element 50 to exert a greater force on one side of the fixation assembly 80 than the other. A portion of the membrane 82 may also be reinforced to cause the fixation element 50 to expand away from the reinforced portion of the membrane 82. Furthermore, the lumen defined by the conductor 44 may have an eccentric profile, or the fixation element 50 may be attached to one side of the conductor 44, to cause the fixation element 50 to expand non-symmetrically with respect to the conductor 44.

In summary, the present invention relates to a cardiac lead that includes a conductive element and a fixation assembly including a threaded member threadably engaged with the conductive element. Rotation of the threaded member causes the threaded member to translate longitudinally relative to the conductive element. A fixation element has a first end coupled to the threaded member and a second end coupled to a fixed location. A resilient membrane is over the fixation element such that rotation of the threaded member affects the resilient membrane radially with respect to the conductive element. A fixation assembly according to the present invention can be deployed in the vasculature of a patient with limited tissue in-growth with the fixation assembly when it is fully expanded. Consequently, if the lead is to be removed from the patient, the fixation assembly may be retracted without damaging the patient's vasculature.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A cardiac lead comprising:
   a conductive element; and
   a fixation assembly including (a) a threaded member threadably engaged with the conductive element such that rotation of the threaded member causes the threaded member to translate longitudinally relative to the conductive element, (b) a fixation element having a first end coupled to the threaded member and a second end coupled to a fixed location, and (c) a resilient membrane extending over the fixation element such that rotation of the threaded member affects the resilient membrane radially with respect to the conductive element.

2. The cardiac lead of claim 1, wherein the threaded member is adapted to engage an actuating device that is operable to rotate the threaded member.

3. The cardiac lead of claim 2, wherein the actuating device comprises a guidewire or stylet.

4. The cardiac lead of claim 1, wherein the threaded member is movable between first and second axial positions relative to the lead body.

5. The cardiac lead of claim 4, wherein the fixation assembly is in a fully collapsed state when the threaded member is at the first axial position, and wherein the fixation assembly is in a fully expanded state when the threaded member is at the second axial position.

6. The cardiac lead of claim 1, wherein the cardiac lead has a proximal end and a distal end, and wherein the fixation assembly is proximate the distal end.

7. The cardiac lead of claim 1, wherein the fixation element comprises a helical structure.

8. The cardiac lead of claim 7, wherein the conductive element comprises a helical structure, and wherein turns of the fixation element are interleaved with turns of the conductive element when the fixation assembly is in a fully collapsed state.

9. A cardiac lead comprising:
   a lead body that defines a passage;
   a conductive element that extends through the passage; and
   a fixation assembly including a threaded member threadably engaged with the conductive element, and an expandable mechanism including a fixation element having a first end coupled to the threaded member and a second end coupled to a fixed location, the expandable mechansism further including a resilient membrane extending over the fixation element, wherein the expandable mechanism is configured to transition between a retracted configuration and an expanded configuration to radially affect the resilient membrane with respect to the lead body when the threaded member is rotated.

10. The cardiac lead of claim 9, wherein the fixation element comprises a helical structure.

11. The cardiac lead of claim 10, wherein the conductive element comprises a helical structure, and wherein turns of the fixation element are interleaved with turns of the conductive element when the fixation assembly is in a fully collapsed state.

12. The cardiac lead of claim 9, wherein the threaded member is adapted to engage an actuating device that is operable to rotate the threaded member.

13. A lead fixation assembly for securing a cardiac lead at a location, the cardiac lead comprising a lead body that defines a passage and a conductive element that extends through the passage, the lead fixation assembly comprising:
a threaded member threadably engaged with the conductive element;
a fixation element having a first end coupled to the threaded member and a second end coupled to a fixed location; and
a resilient membrane extending over the fixation element such that manipulation of the threaded member affects the resilient membrane radially with respect to the lead body.

14. The lead fixation assembly of claim 13, wherein the threaded member is movable between first and second axial positions relative to the lead body.

15. The lead fixation assembly of claim 14, wherein the fixation assembly is in a fully collapsed state when the threaded member is at the first axial position, and wherein the fixation assembly is in a fully expanded state when the threaded member is at the second axial position.

16. The lead fixation assembly of claim 14, wherein rotation of the threaded member causes the threaded member to move between the first and second axial positions.

17. The lead fixation assembly of claim 13, wherein the threaded member is adapted to engage an actuating device that is operable to rotate the threaded member.

18. The lead fixation assembly of claim 13, wherein the fixation element comprises a helical structure.

19. The lead fixation assembly of claim 18, wherein the conductive element comprises a helical structure, and wherein turns of the fixation element are interleaved with turns of the conductive element when the fixation assembly is in a fully collapsed state.

* * * * *